(12) United States Patent
Shin et al.

(10) Patent No.: US 8,814,927 B2
(45) Date of Patent: Aug. 26, 2014

(54) PARTIALLY BIODEGRADABLE STENT

(75) Inventors: Kyong-Min Shin, Seoul (KR); Byung Cheol Myung, Goyang-si (KR); Yong-Hyuni Won, Incheon-si (KR); Tae-won Kim, Kimpo-si (KR)

(73) Assignees: Taewoong Medical Co., Ltd., Seoul (KR); Kyong-Min Shin, Seoul (KR)

( * ) Notice: Subject to any disclaimer, the term of this patent is extended or adjusted under 35 U.S.C. 154(b) by 671 days.

(21) Appl. No.: 12/577,963

(22) Filed: Oct. 13, 2009

(65) Prior Publication Data

US 2010/0211157 A1    Aug. 19, 2010

(30) Foreign Application Priority Data

Feb. 19, 2009    (KR) .................. 10-2009-0013901

(51) Int. Cl.
*A61F 2/06*    (2013.01)
(52) U.S. Cl.
USPC ....................................... 623/1.15; 623/1.16
(58) Field of Classification Search
USPC ........... 623/1.12, 1.13, 1.15, 1.16, 1.24, 1.25, 623/1.26, 1.28, 1.3, 2.1, 2.4, 2.14, 23.68; 606/151, 153
See application file for complete search history.

(56) References Cited

U.S. PATENT DOCUMENTS

| | | | |
|---|---|---|---|
| 5,938,697 A * | 8/1999 | Killion et al. ................ 623/1.15 |
| 6,331,188 B1 * | 12/2001 | Lau et al. ..................... 623/1.13 |
| 6,350,277 B1 * | 2/2002 | Kocur .......................... 623/1.11 |
| 2003/0078649 A1 * | 4/2003 | Camrud et al. .............. 623/1.16 |
| 2007/0055365 A1 * | 3/2007 | Greenberg et al. .......... 623/1.44 |
| 2007/0288084 A1 * | 12/2007 | Lee et al. ..................... 623/1.16 |

* cited by examiner

*Primary Examiner* — Tuan V Nguyen
(74) *Attorney, Agent, or Firm* — Jordan and Hamburg LLP (57) ABSTRACT

A partially biodegradable stent includes a main net body of hollow cylindrical shape formed of elastically deformable wires interlaced with each other, the net body extending in a longitudinal direction and terminating at open opposite ends, and an auxiliary net portion provided at one of the open opposite ends of the main net body, the auxiliary net portion formed of a biodegradable wire which can be degraded and removed by a bodily fluid. The auxiliary net portion is formed by interlacing the biodegradable wire into a cylindrical shape independently of the main net body or by interlacing the biodegradable wire with the elastically deformable wires at one of the open opposite ends of the main net body.

8 Claims, 10 Drawing Sheets

PARTIALLY BIODEGRADABLE STENT

FIELD OF THE INVENTION

The present invention relates to a partially biodegradable stent and, more specifically, to a stent for use in expanding the stenosed part of the bile duct or other bodily organs to assure smooth flow of a bodily fluid such as bile juice or the like. The stent is designed to partially protrude into the duodenum so as to prevent reflux of food into the bile duct from the duodenum and is capable of being partially degraded and removed by a bodily fluid during its use so as to prevent the stent from clogging with food particles.

BACKGROUND OF THE INVENTION

In general, various kinds of stents have been used to expand the stenosed part of the bile duct, the esophagus, the respiratory tract, the ureter or other bodily organs. The stenosed part is generated by a cancer or other diseases or by an inflammation attributable to the use of an endoscope in medical treatment.

Along with the development of medical science, the stents are used in many different fields such as endoscopic retrograde biliary drainage (ERBD), endoscopic retrograde pancreatic drainage (ERPD) and so forth.

Figure 1:
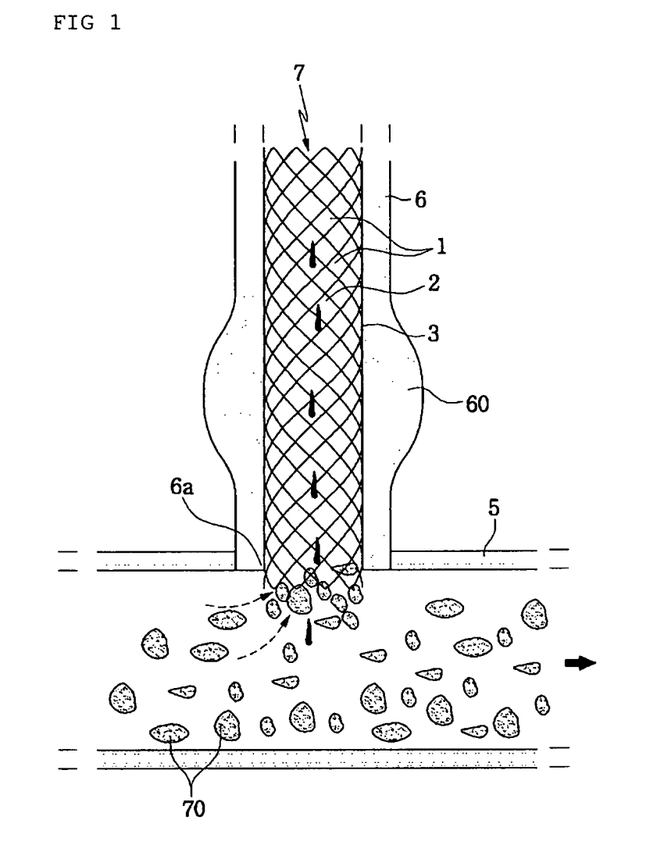
FIG. 1 is a section view illustrating a state that food particles flow backwards into the bile duct from the duodenum in a conventional stent.
Figure 2:
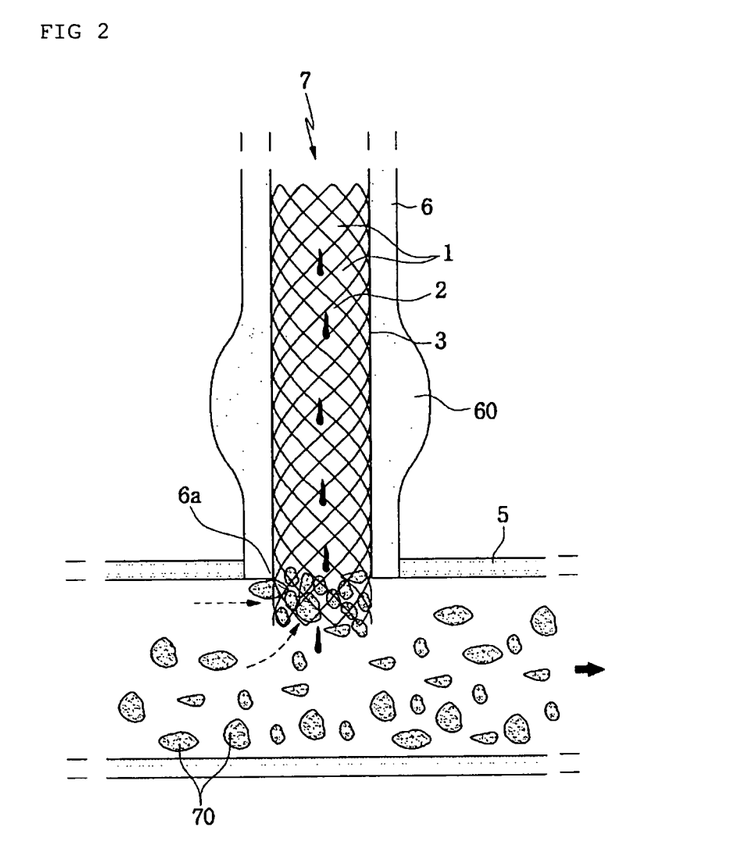
FIG. 2 is a section view illustrating the conventional stent situated inside the bile duct, wherein the stent clogs with food particles.

One typical example of the conventional stents is illustrated in FIGS. 1 and 2. The stent 7 is produced by interlacing super-elastic shape-memory alloy wires 1 into a hollow cylindrical net body 3 with a multiplicity of rhombic meshes 2.

The stent 7 shown in FIGS. 1 and 2 is inserted into the bile duct 6 extending between the liver and the duodenum 5 through the use of a catheter (not shown). The stent 7 thus inserted serves to expand the stenosed part 60 of the bile duct 6, thereby assuring smooth flow of bile juice into the duodenum 5.

The stent 7 is situated in place so that a portion thereof can protrude into the duodenum 5 through the Oddi's sphincter 6a of the bile duct 6. If the stent 7 protrudes a short distance into the duodenum 5 as illustrated in FIG. 1, the food passing through the duodenum 5 may flow backwards into the bile duct 6. In contrast, if the stent 7 protrudes a long distance into the duodenum 5 as illustrated in FIG. 2, the particles 70 of food may be caught in the meshes 2 of the protruding portion of the stent 7. This may sometimes leads to a problem in that the outlet of the bile duct 6 clogs with the particles 70 of food, consequently hindering smooth discharge of bile juice.

SUMMARY OF THE INVENTION

In view of the above-noted and other problems inherent in the prior art, it is an object of the present invention to provide a partially biodegradable stent for expanding the stenosed part of the bile duct or other bodily organs to assure smooth flow of a bodily fluid.

Another object of the present invention is to provide a partially biodegradable stent capable of preventing reflux of food into the bile duct from the duodenum through the Oddi's sphincter.

A further object of the present invention is to provide a partially biodegradable stent capable of being partially degraded and removed by a bodily fluid during its use so as to prevent the stent from clogging with food particles.

In accordance with the present invention, there is provided a partially biodegradable stent including: a main net body of hollow cylindrical shape formed of elastically deformable wires interlaced with each other, the net body extending in a longitudinal direction and terminating at open opposite ends; and an auxiliary net portion provided at one of the open opposite ends of the main net body, the auxiliary net portion formed of a biodegradable wire which can be degraded and removed by a bodily fluid.

With the partially biodegradable stent of the present invention, it is possible to expand the stenosed part of the bile duct or other bodily organs to assure smooth flow of a bodily fluid. The stent of present invention can prevent reflux of food into the bile duct from the duodenum through the Oddi's sphincter. In addition, the stent of present invention can be partially degraded and removed by a bodily fluid during its use so as to prevent the stent from clogging with food particles.

BRIEF DESCRIPTION OF THE DRAWINGS

The above and other objects and features of the present invention will become apparent from the following description of preferred embodiments, given in conjunction with the accompanying drawings.

DETAILED DESCRIPTION OF THE PREFERRED EMBODIMENTS

Preferred embodiments of a partially biodegradable stent in accordance with the present invention will now be described in detail with reference to the accompanying drawings. The partially biodegradable stent can be used in expanding different bodily tracts or ducts such as the bile duct, blood vessels and the like. Hereinafter, description will be made on an instance where the stent is used in expanding the stenosed part of the bile duct.

Figure 3:
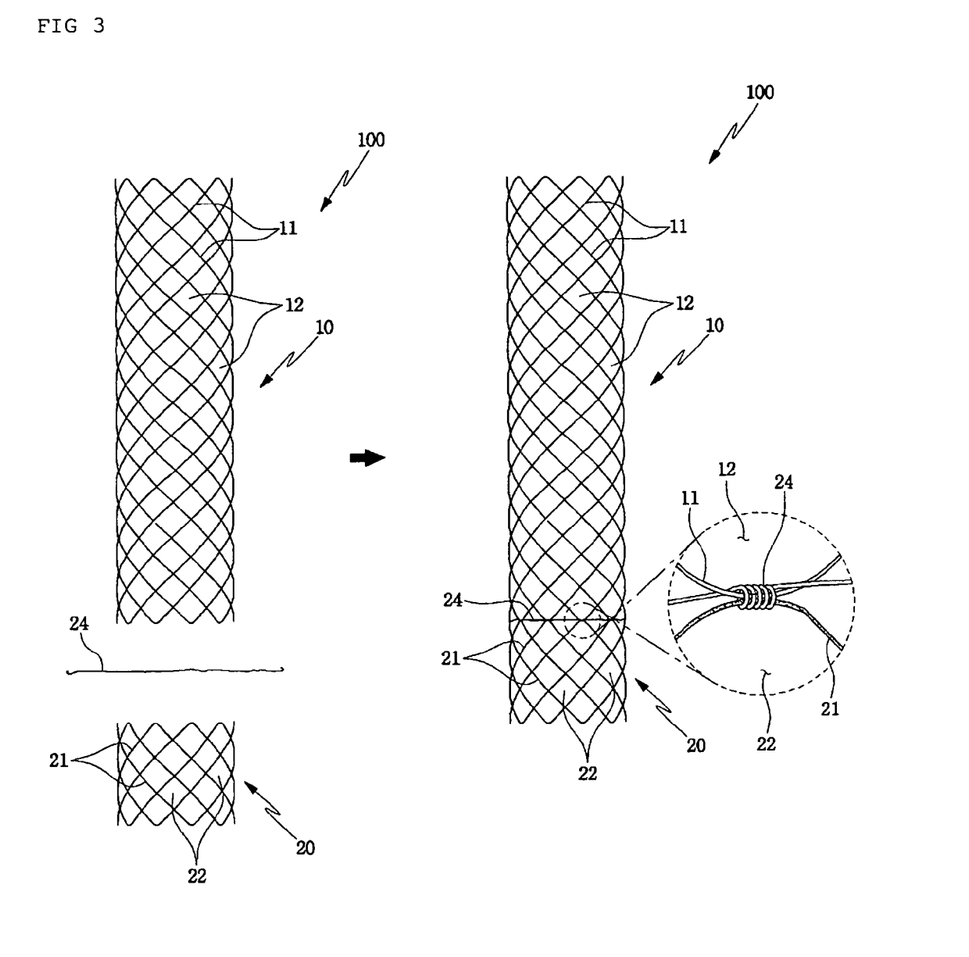
FIG. 3 shows a partially biodegradable stent in accordance with one embodiment of the present invention, wherein the stent includes a main net body made of a shape-memory alloy, an auxiliary net portion made of a biodegradable material and a binding wire for tying the main net body and the auxiliary net portion together.

Referring first to FIG. 3, there is shown a partially biodegradable stent 100 in accordance with one embodiment of the present invention. The stent 100 includes a main net body 10 of hollow cylindrical shape formed of elastically deformable wires 11 interlaced with each other. The main net body 10 extends in the longitudinal direction of the stent 100 and terminates at open opposite ends. When forming the main net body 10, the elastically deformable wires 11 are interlaced with each other to leave a multiplicity of rhombic meshes 12 therebetween.

The length and diameter of the main net body 10 may be appropriately selected depending on the size of the stenosed part of the bile duct. The elastically deformable wires 11 are preferably made of an ultra elastic alloy such a shape-memory alloy or the like so that the stent 100 can be self-expanded radially outwards when situated inside the bile duct.

The stent 100 further includes an auxiliary net portion 20 provided at one of the open opposite ends of the main net body 10. The auxiliary net portion 20 protrudes into the duodenum when the stent 100 is situated inside the bile duct. This is to prevent the food from flowing backwards into the bile duct from the duodenum.

Unlike the main net body 10, the auxiliary net portion 20 is formed of a biodegradable wire 21 which can be degraded and removed over a specified time period by a bodily fluid such as bile juice, gastric acid, saliva or other fluids secreted from the body. The biodegradable wire 21 is preferably made of a biodegradable polymer, e.g., poly-L-lactic acid, poly-lactic acid, poly-glycolic acid, poly-glycolide-co-L-lactide acid, polydioxanone, poly-glycolide-co-caprolactone or other like substances. One or more of these substances may be used independently or in combination.

When forming the auxiliary net portion 20, the biodegradable wire 21 is interlaced into a cylindrical shape independently of the main net body 10 so as to leave a multiplicity of rhombic meshes 12. The length and diameter of the auxiliary net portion 20 may be appropriately selected depending on the diameter of the duodenum into which it protrudes. More precisely, the length and diameter of the auxiliary net portion 20 is set to assure smooth movement of the food through the duodenum while preventing reflux of the food into the bile duct.

In the embodiment illustrated in FIG. 3, the stent 100 further includes a binding wire 24 for tying the main net body 10 and the auxiliary net portion 20 together. The main net body 10 and the auxiliary net portion 20 are tied together by the binding wire 24 to produce the stent 100. The binding wire 24 may be formed of either an elastically deformable wire or a biodegradable wire.

Figure 4:
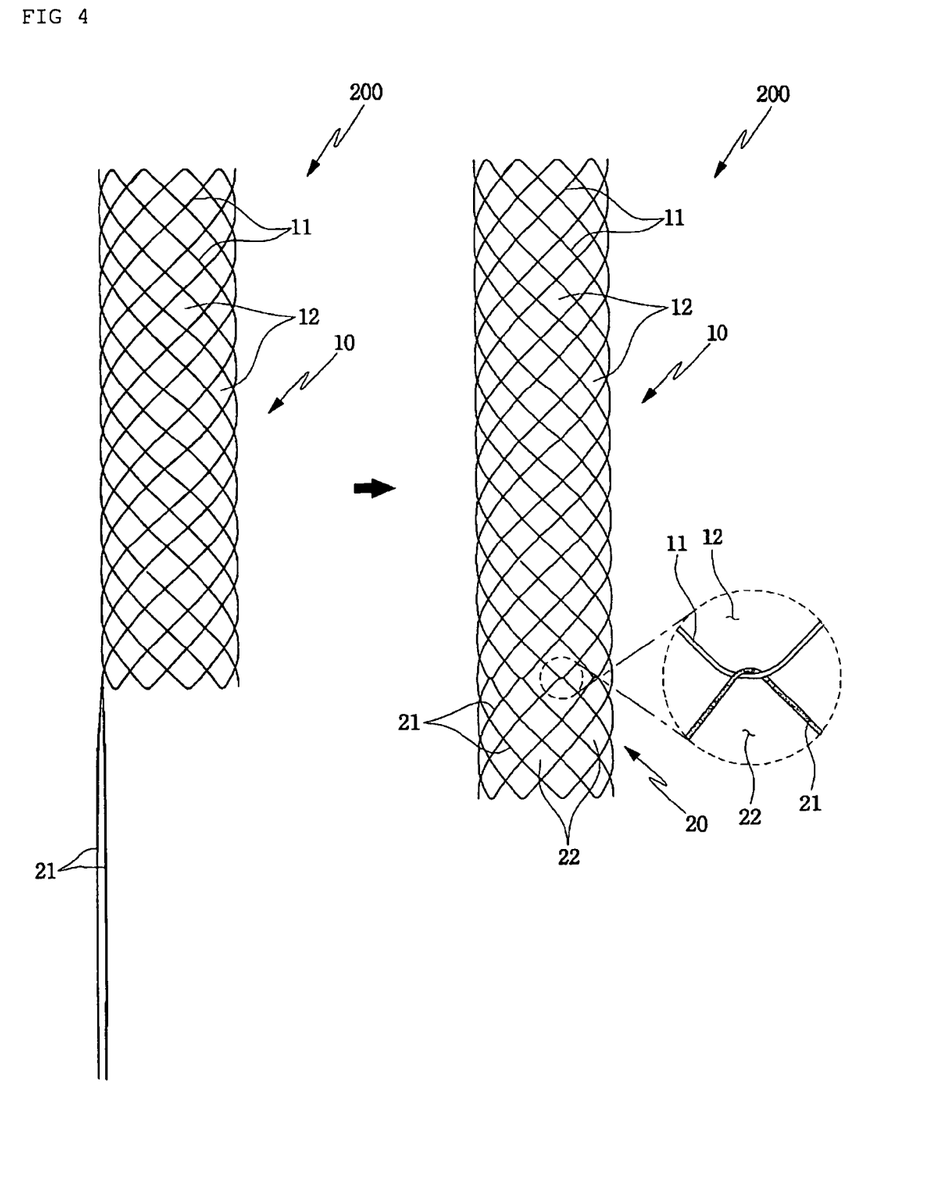
FIG. 4 shows a partially biodegradable stent in accordance with another embodiment of the present invention, wherein the stent includes a main net body formed of elastically deformable wires and an auxiliary net portion formed by directly interlacing a biodegradable wire with the wires of the main net body.

Referring next to FIG. 4, there is shown a partially biodegradable stent 200 in accordance with another embodiment of the present invention. The stent 200 includes a main net body 10 of hollow cylindrical shape formed of elastically deformable wires 11 interlaced with each other. The main net body 10 extends in the longitudinal direction of the stent 200 and terminates at open opposite ends. When forming the main net body 10, the elastically deformable wires 11 are interlaced with each other to leave a multiplicity of rhombic meshes 12 therebetween.

The length and diameter of the main net body 10 may be appropriately selected depending on the size of the stenosed part of the bile duct. The elastically deformable wires 11 are preferably made of an ultra elastic alloy such a shape-memory alloy or the like so that the stent 200 can be self-expanded radially outwards when situated inside the bile duct.

The stent 200 further includes an auxiliary net portion 20 provided at one of the open opposite ends of the main net body 10. The auxiliary net portion 20 protrudes into the duodenum when the stent 200 is situated inside the bile duct. This is to prevent the food from flowing backwards into the bile duct from the duodenum.

Unlike the main net body 10, the auxiliary net portion 20 is formed of a biodegradable wire 21 which can be degraded and removed over a specified time period by a bodily fluid such as bile juice, gastric acid, saliva or other fluids secreted from the body. The biodegradable wire 21 is preferably made of a biodegradable polymer, e.g., poly-L-lactic acid, poly-lactic acid, poly-glycolic acid, poly-glycolide-co-L-lactide acid, polydioxanone, poly-glycolide-co-caprolactone or other like substances. One or more of these substances may be used independently or in combination.

In the embodiment illustrated in FIG. 4, the auxiliary net portion 20 is formed by interlacing the biodegradable wire 21 with the elastically deformable wires 11 at one of the open opposite ends of the main net body 10. At this time, the biodegradable wire 21 is interlaced into a cylindrical shape so as to leave a multiplicity of rhombic meshes 12. The length and diameter of the auxiliary net portion 20 is set to assure smooth movement of the food through the duodenum while preventing reflux of the food into the bile duct. It is preferred that the diameter of the auxiliary net portion 20 is equal to the diameter of the main net body 10.

Figure 5:
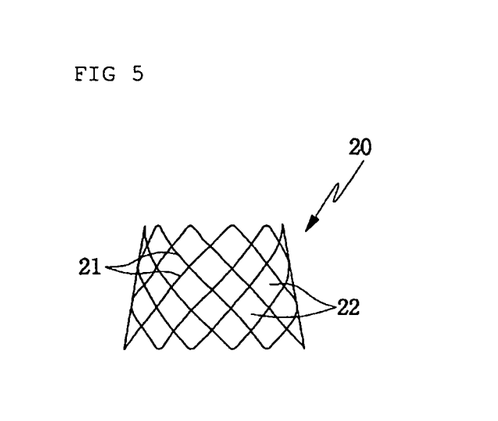
FIGS. 5 and 6 are views showing other different examples of the auxiliary net portion.
Figure 10:
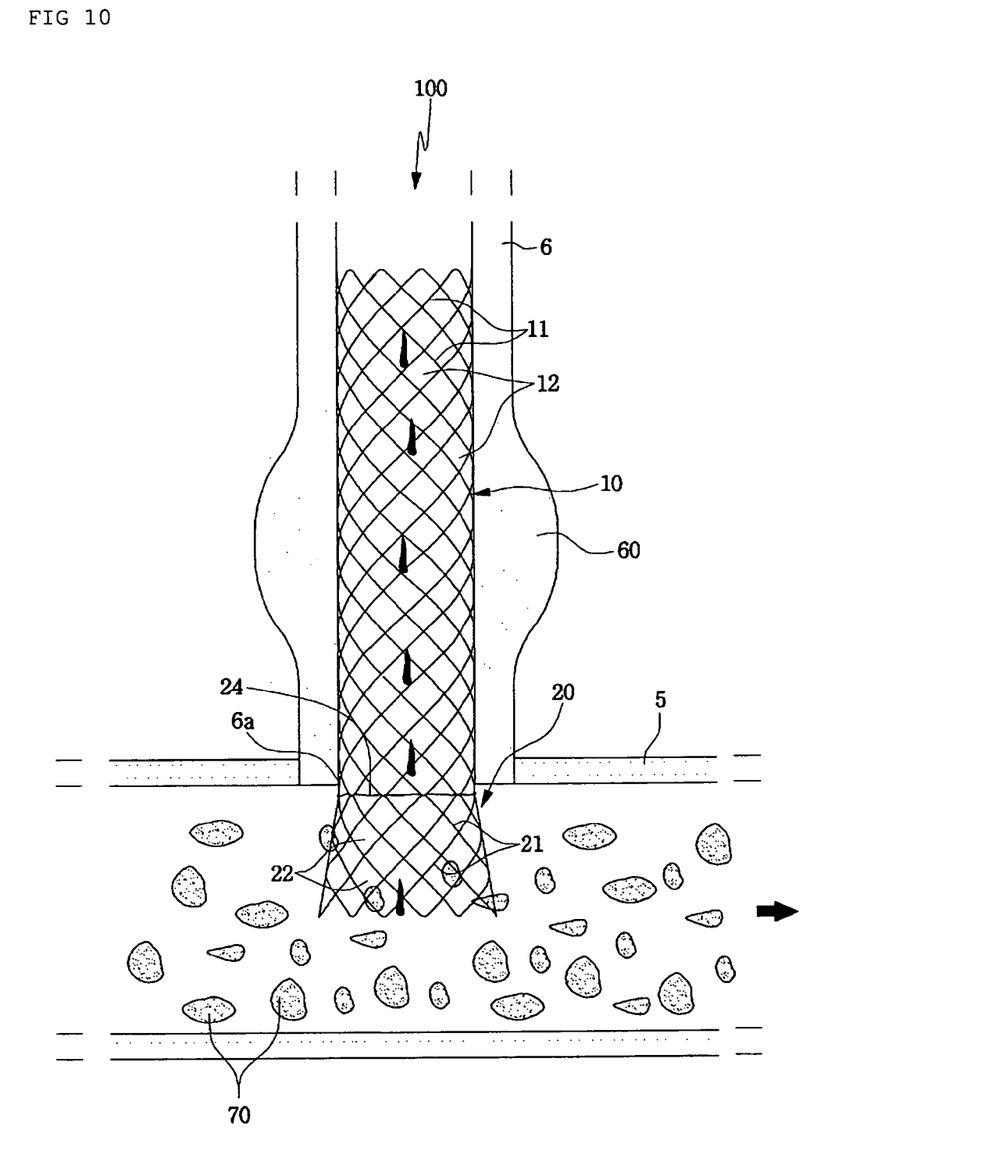
FIG. 10 is a section view illustrating the stent situated inside the stenosed portion of the bile duct, which stent is provided with the auxiliary net portion shown in FIG. 5.

Referring to FIG. 5, there is shown one modified example of the auxiliary net portion 20 which includes a biodegradable wire 21 interlaced to leave a multiplicity of rhombic meshes 22 therebetween. is formed of an interlaced biodegradable wire 21. This auxiliary net portion 20 has a diameter gradually becoming larger away from the main net body 10. In other words, the auxiliary net portion 20 is tapered so that it can has an open tip end greater in diameter than its base end to be connected to the main net body 10. As can be seen in FIG. 10, the auxiliary net portion 20 of this shape protrudes into the duodenum 5 when the stent 100 is situated inside the stenosed part 60 of the bile duct 6. Thus the auxiliary net portion 20 helps prevent the food particles 70 from flowing backwards into the bile duct 6.

Figure 6:
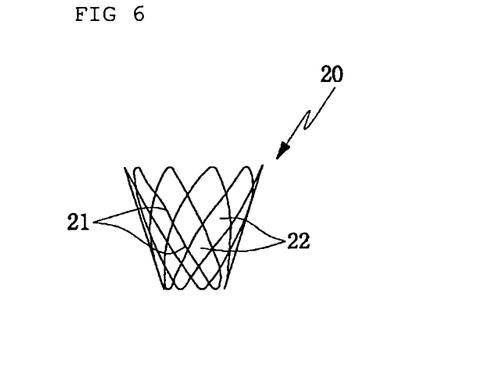
Figure 11:
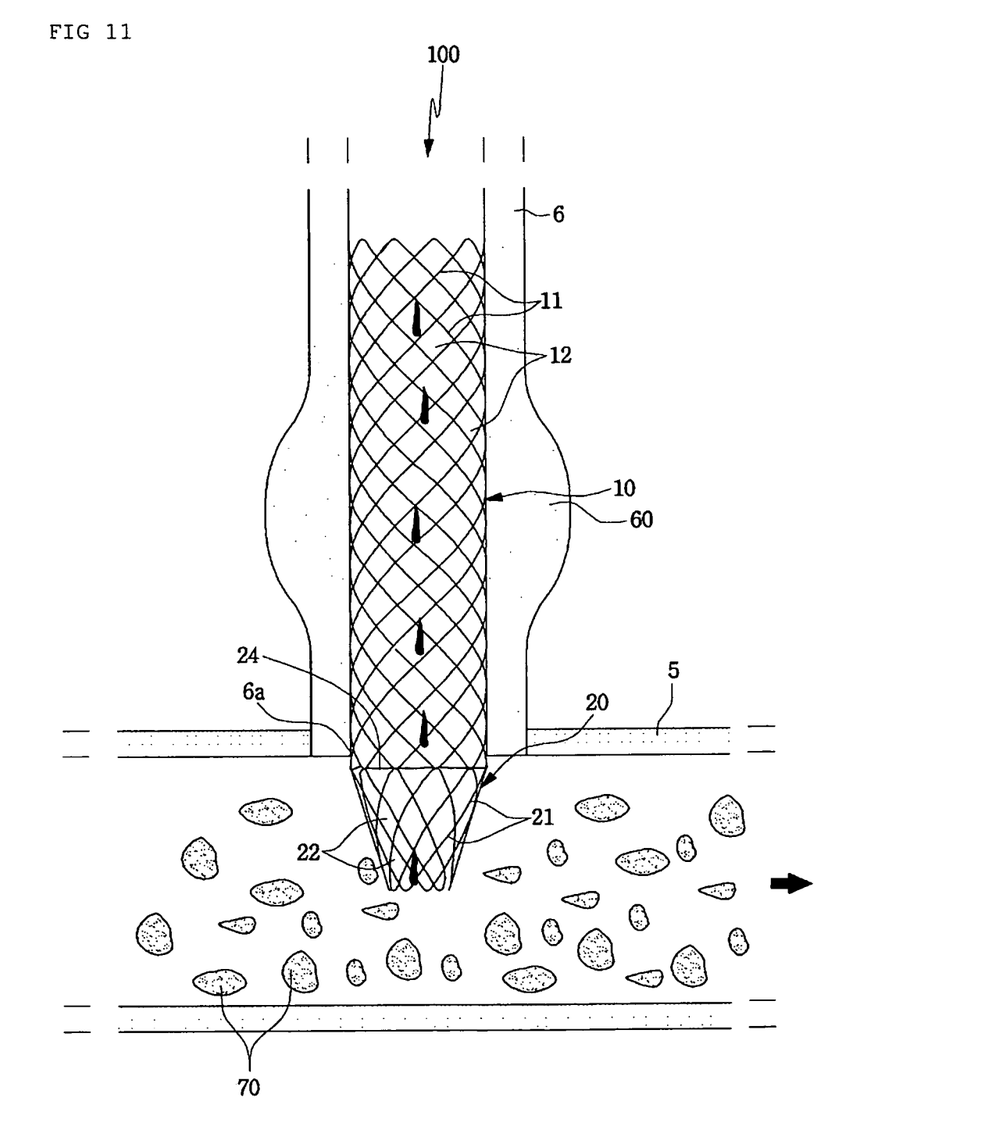
FIG. 11 is a section view illustrating the stent situated inside the stenosed portion of the bile duct, which stent is provided with the auxiliary net portion shown in FIG. 6.

Referring to FIG. 6, there is shown another modified example of the auxiliary net portion 20 which includes a biodegradable wire 21 interlaced to leave a multiplicity of rhombic meshes 22 therebetween. As opposed to the auxiliary net portion 20 shown in FIG. 5, this auxiliary net portion 20 has a diameter gradually becoming smaller away from the main net body 10. In other words, the auxiliary net portion 20 is tapered so that it can has an open tip end smaller in diameter than its base end to be connected to the main net body 10. As can be seen in FIG. 11, the auxiliary net portion 20 of this shape protrudes into the duodenum 5 when the stent 100 is situated inside the stenosed part 60 of the bile duct 6. Thus the auxiliary net portion 20 helps prevent the food particles 70 from flowing backwards into the bile duct 6.

Figure 7:
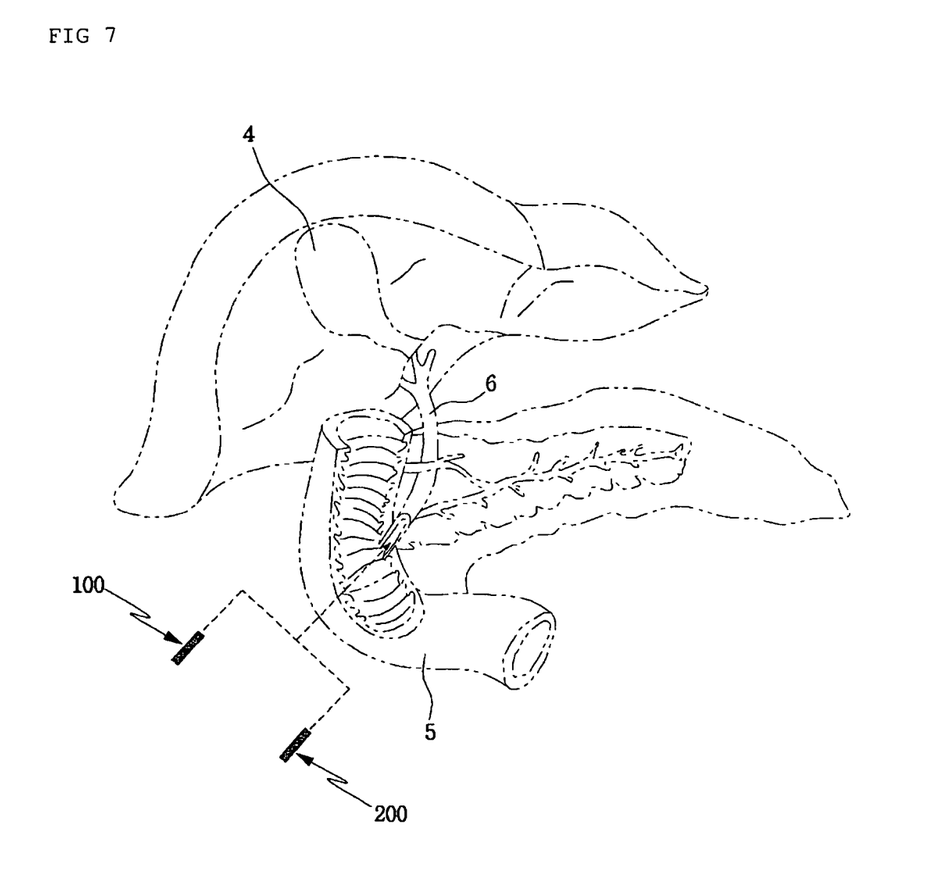
FIG. 7 is a schematic view illustrating a process of inserting the present stent into the bile duct.

Turning to FIG. 7, the partially decomposable stent 100 or 200 set forth above is situated inside the stenosed portion of the bile duct 6 through which the bile juice secreted from the gallbladder 4' of the liver 4 flows into the duodenum 5.

An endoscope and a catheter well-known in the art are used in inserting the stent 100 or 200 into the bile duct 6. More specifically, the catheter holding the stent 100 or 200 is inserted into the bile duct 6 through the duodenum 5, at which time the operator drives the catheter to a desired position while observing the movement of the catheter with the endoscope.

Figure 8:
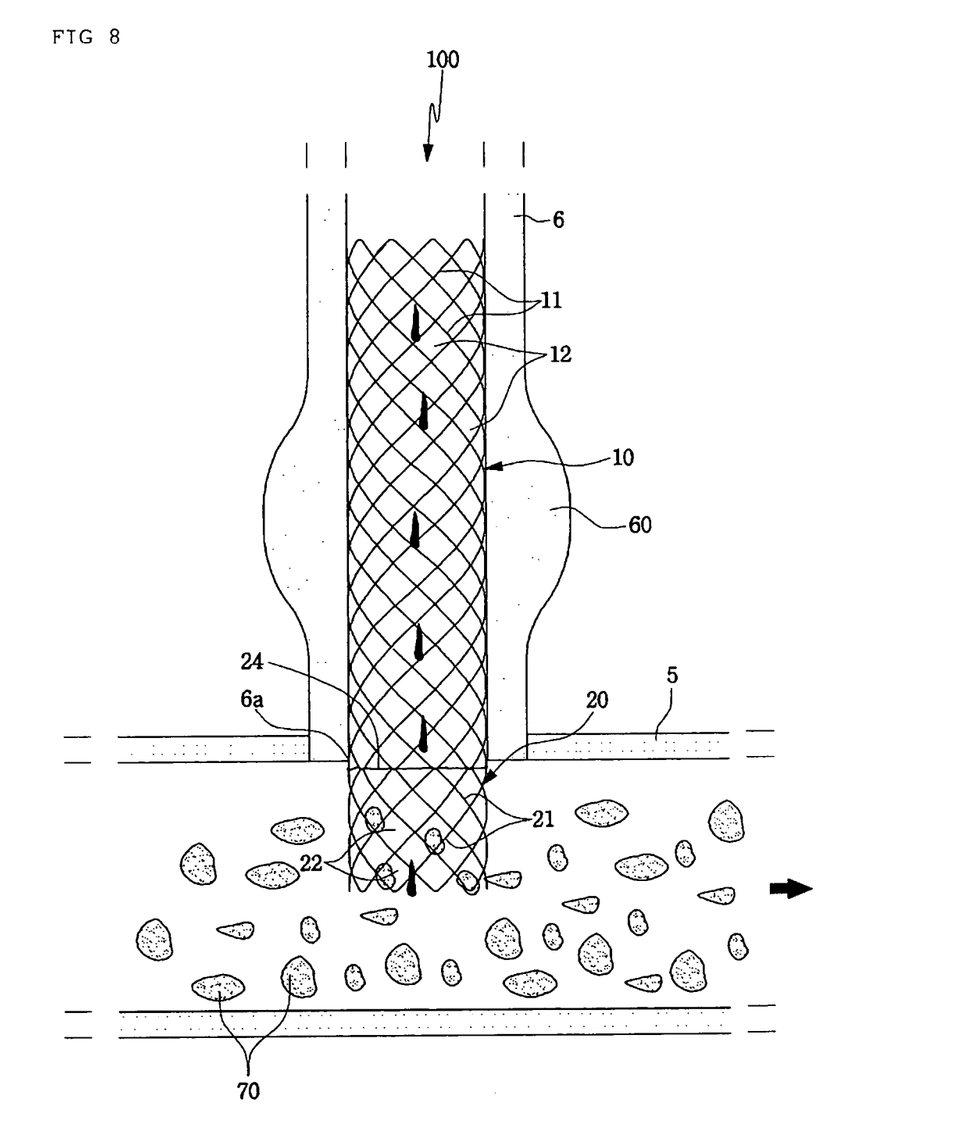
FIG. 8 is a section view illustrating the present stent situated inside the stenosed portion of the bile duct, with the auxiliary net portion protruding into the duodenum.

When the catheter reaches a desired position, i.e., the stenosed part 60 of the bile duct 6, the stent 100 or 200 is released from the catheter and is situated inside the bile duct 6 so that the main net body 10 can expand the stenosed part 60 and the Oddi's sphincter 6a of the bile duct 6 with the auxiliary net portion 20 protruding into the duodenum 5, as shown in FIG. 8. In this state, the bile juice is smoothly excreted into the duodenum 5 through the bile duct 6. Since the auxiliary net portion 20 protrudes into the duodenum 5, the food particles 70 are prevented from flowing backwards into the bile duct 6.

Figure 9:
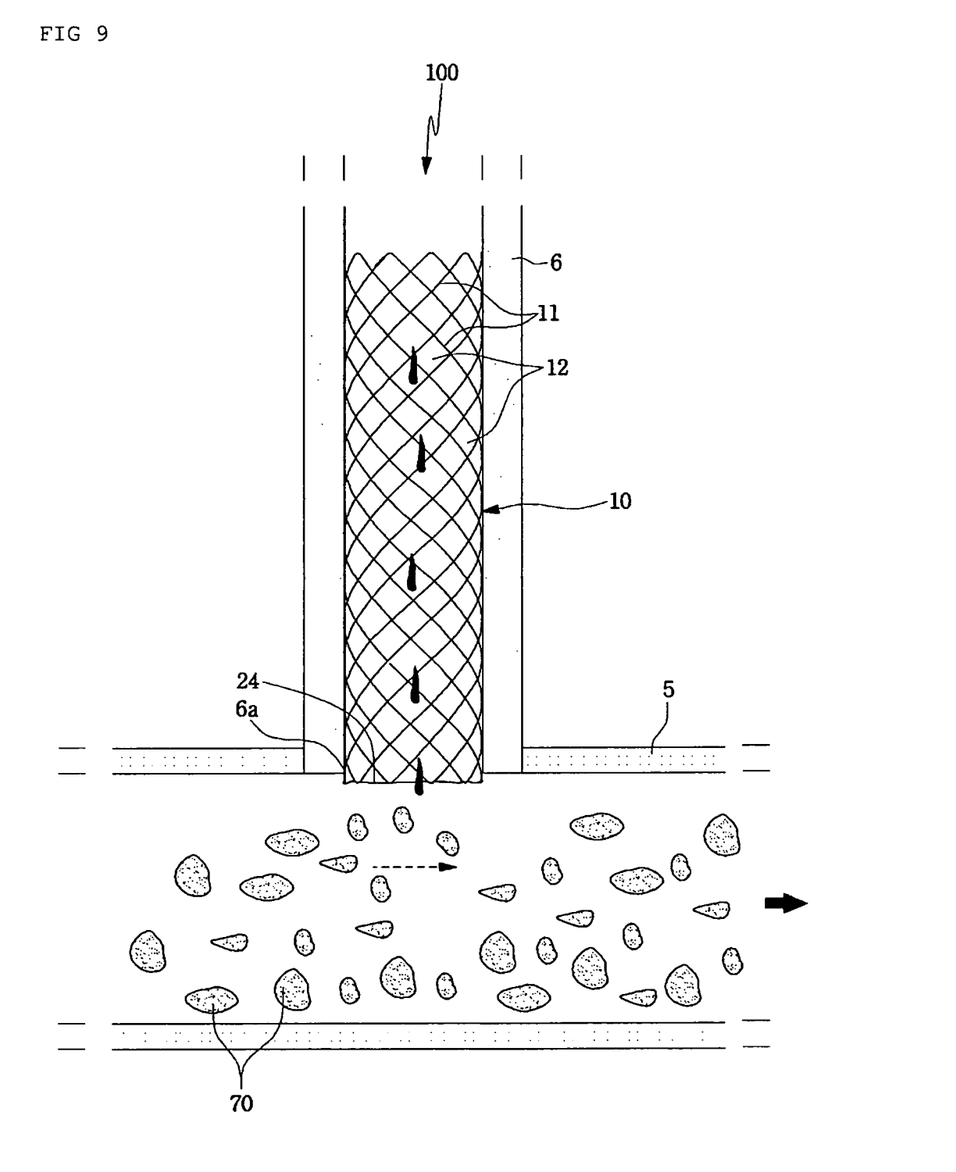
FIG. 9 is a section view illustrating the present stent situated inside the stenosed portion of the bile duct, with the auxiliary net portion degraded and removed by a bodily fluid.

It is sometimes the case that the auxiliary net portion 20 clogs with the food particles 70 over time, consequently hindering the excretion of the bile juice into the duodenum 5. In the present invention, the auxiliary net portion 20 is formed of biodegradable wire 21. Therefore, as illustrated in FIG. 9, the auxiliary net portion 20 is degraded and removed by a bodily fluid bile juice, gastric acid, saliva or other fluids secreted from the body, after a specified time period has lapsed. The main net body 10 continues to be situated inside the bile duct 6. This eliminates the possibility that the auxiliary net portion 20 clogging with the food particles 70 remains attached to the main net body 10 and hinders the excretion of the bile juice into the duodenum 5.

While certain embodiments of the present invention have been described hereinabove, the present invention shall not be limited thereto. It will be understood by those skilled in the art that various changes and modifications may be made without departing from the scope of the invention defined in the claims.

What is claimed is:

1. A partially biodegradable stent comprising:
   a main net body of hollow cylindrical shape formed of elastically deformable wires interlaced in a predetermined pattern, the net body extending in a longitudinal direction and terminating at open opposite ends; and
   an auxiliary net portion provided at one of the open opposite ends of the main net body, the auxiliary net portion formed of a biodegradable wire interlaced in the predetermined pattern, which can be degraded and removed by a bodily fluid, wherein the auxiliary net portion is formed by interlacing the biodegradable wire into a cylindrical shape independently of the main net body, and further comprising a binding wire for tying the main net body and the auxiliary net portion together.

2. The stent as recited in claim 1, wherein the auxiliary net portion has a diameter gradually becoming larger away from the main net body.

3. The stent as recited in claim 1, wherein the auxiliary net portion has a diameter gradually becoming smaller away from the main net body.

4. The stent as recited in claim 1, wherein the elastically deformable wires are made of a shape-memory alloy.

5. The stent as recited in claim 1, wherein the biodegradable wire is made of a biodegradable polymer selected from the group consisting of poly-L-lactic acid, poly-lactic acid, poly-glycolic acid, poly-glycolide-co-L-lactide acid, poly-dioxanone and poly-glycolide-co-caprolactone.

6. A partially biodegradable stent comprising:
   a main net body of hollow cylindrical shape formed of elastically deformable wires interlaced with each other, the net body extending in a longitudinal direction and terminating at open opposite ends; and
   an auxiliary net portion provided at one of the open opposite ends of the main net body, the auxiliary net portion formed of a biodegradable wire which can be degraded and removed by a bodily fluid, wherein the auxiliary net portion has a diameter gradually becoming larger away from the main net body, the auxiliary net portion formed by interlacing the biodegradable wire into a cylindrical shape independently of the main net body;
   and a binding wire tying the main net body and the auxiliary net portion together.

7. The stent as recited in claim 6, wherein the elastically deformable wires are made of a shape-memory alloy.

8. The stent as recited in claim 6, wherein the biodegradable wire is made of a biodegradable polymer selected from the group consisting of poly-L-lactic acid, poly-lactic acid, poly-glycolic acid, poly-glycolide-co-L-lactide acid, poly-dioxanone and poly-glycolide-co-caprolactone.

* * * * *